United States Patent
Pompidou et al.

(10) Patent No.: US 8,969,010 B2
(45) Date of Patent: Mar. 3, 2015

(54) IN VIVO MICRO-INVASIVE INVESTIGATION DEVICE INCLUDING A METAL GUIDE

(75) Inventors: Alain Pompidou, Brussels (BE); Albert-Claude Benhamou, Paris (FR)

(73) Assignee: Biostems Ltd, Dublin (IE)

( * ) Notice: Subject to any disclaimer, the term of this patent is extended or adjusted under 35 U.S.C. 154(b) by 1225 days.

(21) Appl. No.: 12/919,655

(22) PCT Filed: Feb. 24, 2009

(86) PCT No.: PCT/EP2009/001308
§ 371 (c)(1),
(2), (4) Date: Jan. 5, 2011

(87) PCT Pub. No.: WO2009/106295
PCT Pub. Date: Sep. 3, 2009

(65) Prior Publication Data
US 2011/0092783 A1 Apr. 21, 2011

(30) Foreign Application Priority Data
Feb. 26, 2008 (EP) .................................. 08290179

(51) Int. Cl.
*G01N 33/53* (2006.01)
*A61B 5/00* (2006.01)
*A61B 5/145* (2006.01)
*A61B 5/1473* (2006.01)

(52) U.S. Cl.
CPC .............. *A61B 5/00* (2013.01); *A61B 5/14542* (2013.01); *A61B 5/1473* (2013.01); *A61B 5/6851* (2013.01); *A61B 2562/02* (2013.01); *A61B 2562/043* (2013.01)
USPC ........................................................ 435/7.1

(58) Field of Classification Search
None
See application file for complete search history.

(56) References Cited

U.S. PATENT DOCUMENTS

| 5,938,595 A | 8/1999 | Glass et al. .................... 600/342 |
| 6,689,604 B1 * | 2/2004 | Gilbert et al. .............. 435/320.1 |
| 7,259,019 B2 * | 8/2007 | Pawliszyn et al. ............. 436/178 |
| 7,291,497 B2 | 11/2007 | Holmes et al. .............. 435/287.2 |
| 7,842,012 B2 * | 11/2010 | Ellis et al. ................. 604/164.13 |
| 2011/0251105 A1 * | 10/2011 | Walt et al. ........................ 506/13 |

FOREIGN PATENT DOCUMENTS

| EP | 0234928 A | 9/1987 | ............. G01N 21/77 |
| EP | 135848 A | 6/2004 | |
| WO | 01/69257 A2 | 9/2001 | ........... G01N 33/543 |

OTHER PUBLICATIONS

International PCT Search Report, PCT/EP2009/001308, 5 pages, Apr. 20, 2009.

* cited by examiner

*Primary Examiner* — Ann Lam
(74) *Attorney, Agent, or Firm* — King & Spalding L.L.P.

(57) ABSTRACT

The invention relates to an analysis device, wherein said system includes at least one metal guide at one end of which is provided at least one series of pits to which are directly coupled reagents specific to a substrate, said end being a perforating one, while the other end is intended for controlling said guide and is optionally associated with a suction system. The guide may be inserted into a protection system that is removable at the level of the functionalized end, up to the micro-analysis and/or micro-sampling site, and/or into a medical instrument having an inner channel in which said guide may slide. The present invention also relates to the use of such a device for making a tool for diagnosing cancer, an inflammation, an infection, a neurodegenerative disease or a graft rejection in a patient, preferably by transparietal delivery. The invention further relates to a method for the ex vivo analysis of a substrate using such a device.

26 Claims, 10 Drawing Sheets

US 8,969,010 B2

IN VIVO MICRO-INVASIVE INVESTIGATION DEVICE INCLUDING A METAL GUIDE

CROSS-REFERENCE TO RELATED APPLICATIONS

This application is a U.S. National Stage Application of International Application No. PCT/EP2009/001308 filed Feb. 24, 2009, which designates the United States of America, and claims priority to EP Application No. 08290179.4 filed Feb. 26, 2008, the contents of which are hereby incorporated by reference in their entirety.

TECHNICAL FIELD

The present invention concerns the functionalization of a transparietal investigation device, a method of ex vivo analysis of a substrate using a functionalized device of the invention, and the use of such a device for the fabrication of a tool for the diagnosis of a cancer, an infection, an inflammation, a neurodegenerative disease or graft rejection in a patient.

BACKGROUND

Investigation or in vivo treatment device are known of the state of the art. Such devices take the form of a rigid tube of endoscope type or of a catheter constituted of a flexible tube which is inserted in the organism, especially by natural pathways or the vessels, and which allows to reach an organ or a specific tissue. These devices allow especially the elimination of blood clot or, when they are associated to optical fibres, the visualisation and the in vivo control of the state of a system, as the digestive tube, or of an organ, as the colon. The traumatism for the patient resulting from the use of such devices is then minimized but still stay to ameliorate. However, it is not always possible to carry out an analysis of the organs or the tissues in a patient with these devices. Such impossibility may result from the reduced accessibility of said tissue or organ compared to the blood circulation or the natural pathways, or from the difficulty to carry out a reliable diagnostic without having recourse to a fine study of the cells of said organ or tissue. In these cases, it is generally used in the state of the art and by now, the sampling of a fragment of said tissue or organ (biopsies) in order to ex vivo control the morphology of these tissues or organs, or more finely the one of their constitutive cells, especially by mean of fine needles (FNA or <<Fine Needle Aspiration>>: Engelstein et al., Br. J. Urol., 7: 210-213, 1994; Rodrigues et al., J. Am. Acad. Dermatol., 42: 735-740, 2000; Ariga et al., Am. J. Surg., 184: 410-413, 2002; Pérez-Guillermo et al., Diagn. Cytopathol., 32: 315-320, 2005; Fernandez-Esparrach et al., Arch. Bronconeomol., 43: 219-224, 2007). Moreover, it is also possible to analyse the expression status of a certain number of markers, the expression of which is correlated with a specific pathologic state (especially cancer, inflammation, infection, neurodegenerative disease or graft rejection).

However, these different methods, because of the sampling of a biopsy or of the aspiration of cells, involve a traumatism, sometimes important, to said tissue or organ and, consequently, to the patient. The organism of the latter may so be sorely afflicted because of haemorrhages or of the cicatrisation consecutively to the sampling, especially for certain organs (brain, pancreas, liver or lung).

It so exists still now a need for the identification of new investigation methodologies allowing to carry out a reliable and accurate diagnostic, especially compared to the expression of markers specifically associated to different pathologies such as cancer, inflammation, infection or neurodegenerative disease, while limiting the traumatisms inflicted to the patient.

The patent EP 1 358 481 describes an device of analysis or of in vivo treatment comprising (i) a micro-system of investigation of a substrate other than by analysis of a fluorescent signal, (ii) a flexible butt to an extremity of which is fixed said micro-system and the other extremity of which is intended to the control of said micro-system, (iii) a medical instrument having an internal opening in which said flexible butt may slide, (iv) a sliding system of protection of the micro-system that is removable on the level with the substrate, and (v) on the level of the said micro-system, a system of dilacerations of tissue or cell, eventually associated with one or several devices chosen among a device for monitoring by remote control by means of sensorial receptors (tactile, optical, physico-chemical or numerized informatic), for carrying out biopsies, for treatment, for local injection of biological or chemical products.

In order to allow the effraction of blood vessels and the dilacerations of tissues or cells, the micro-system is so associated with another more rigid system ensuring this function, preferably in distal position.

However, in the case of an in vivo investigation device, the investigation device is the more often directed to the target organ or tissue by using the endovascular or endocavitary pathway. The coupling of the micro-system with a dilaceration system then increases in a non-negligible manner the diameter at the extremity of the described device. The latter then reveal itself to be of a too complex use to be correctly directed to its target site without altering simultaneously the blood circulation pathways. Simultaneously, the coupling of multiple elements do harm to the general flexibility of the device, and so to its correct guidance, as to the obtention of the rigidity, necessary to allow the perforation of an organ or a tissue.

SUMMARY

Following important researches, the inventor has now managed to develop an device comprising a metallic guide to a perforating extremity of which are directly coupled reactive groups, especially antibodies or antibody fragments, specific of a substrate to be tested, and the other extremity of which is intended to the manoeuvring of said guide from the insertion site to the site of micro-analysis and/or micro-sampling of said substrate. Said guide may be inserted into a removable protection system, for example a flexible catheter, then allowing to protect the functionalised extremity of said guide to the site of micro-analysis and/or micro-sampling of the substrate to be tested constitutive of the tissue, the organ or the cells of these ones.

The invention is to structure the surface of the guide in order to define some spots on the guide, for example wells, where the reactive groups will be deposited and where the biochemical interactions will occur. Said "wells" may be carried out by different methods such as by lithography by Focused Ion Beam (FIB or for <<Focused Ion beam>>: Xie et al., Nuclear Instruments & Methods in Physics research Section B-beam Interactions with Materials and Atoms, 211(3): 363-368, 2003), by laser lithography followed by an electrochemical attack and a laser.

Alternatively, the structuration of the metallic guide may be carried out in order to define some spots on said guide, for example at least one furrow in which is jointly associated at least one miniaturized biochip, linear, circular or in the form of a ribbon, where the reactive groups will be deposited and where the biochemical reactions will occur. The spots formed by structuration of the surface of the guide, for example wells, do not form relief at the surface of the guide, but some furrows, or hollows. The spots formed by the structuration of the surface of the guide so do not increase the diameter of the guide.

Advantageously, the spots formed by the structuration of the surface of the guide are situated at the surface of the guide, which means that these spots are directly in contact with the fluids, the tissues and the cells.

Moreover, said device may be inserted in a medical instrument having an internal opening in which said metallic guide may slide, and especially in a transparietal needle punction, especially transcutaneous or transmucosal, or an endoscope, including an endovascular system of navigation.

Moreover, said device may be associated with an optical fibre, or the metallic guide of said device may be replaced by an optical fibre, a perforating extremity of which is associated to a metallic ring on which are directly coupled reactive groups, especially antibodies or antibody fragments, specific of a substrate to be tested, so allowing a fine in situ visualization, in view of the in vivo capture of the elements necessary to the diagnostic and eventually to the prognosis evaluation. The properties of the optical fibre are used for purposes of marking imagery and of setting of the device from the in situ visualization.

The device according to the invention, because of its simplification presents, while staying micro-invasive, a flexibility or elasticity improved compared to the devices of the prior art. The latter then may be used much more efficiently for an investigation by endocavitary pathway, especially by endovascular pathway, or by transparietal pathway, especially by transcutaneous or transmucosal pathway. Moreover, the device according to the invention, because of the use of a metallic guide, an extremity of which is coupled to specific reagents, is rigid enough at its functionalized extremity to efficiently perforate a tissue or an organ. Finally, the diameter of the device according to the invention at its extremity is weak enough to allow the simplified navigation in the blood circulation or in the natural cavities, and particularly to minimize the traumatism at the level of the tissue or the organ that the latter must perforate.

Moreover, and after the withdrawal of the device, it is so possible to ex vivo identify by means of standard methods, as an immunoenzymatic dosage or by immunofluorescence, for example on a solid support [ELISA technique, protein chips (ESPINA et al., J. Immunol. Methods, vol. 290, p: 121-133, 2004)], the presence and the relative concentration of said specific substrate(s) at the extremity of the device according to the invention and so at the level of the site of micro-analysis ad/or micro-sampling (organ or tissue).

Lastly, and because of the nature of the metallic guide, the device presents an improved imagery signal (arteriography, echography, scan, MRI, etc. . . . ). This property allows to considerably simplify the radioguidance of the device according to the invention at the time of the intervention to the target tissue or organ. It is the same thing for the coupling of said device with an optical fibre for the purpose of marking imagery, which allows the fine in situ visualization.

Consequently, a first object of the invention is a device for the analysis of a substrate, characterized in that it comprises a micro-invasive system of investigation and/or of micro-sampling of said substrate, said system being constituted of at least one metallic guide to an extremity Ea of which is provided with at least one series of wells to which is directly coupled at least one reactive group specific of said substrate, said functionalized extremity Ea being perforating, and the other extremity Em of which is intended to the manoeuvring of said metallic guide and eventually associated with an aspiration system.

Advantageously, the surface of the extremity Ea may be structured so as to define at least one series of wells to which is directly coupled at least one reactive group specific of said substrate, said extremity Ea being perforating.

The device according to the invention, because of the weak traumatism that it causes to the patient, allows to carry out several micro-analyses or micro-samplings to a patient at regular intervals (for example, analyses and/or samplings carried out in stages within the prostate). Said analyses and/or successive samplings so allow, in addition to the diagnosis, to follow the evolution of a cancer, an inflammation, an infection, a neurodegenerative disease or the good graft retention of an organ in a patient.

Advantageously, the functionalized extremity Ea may present on a length of about 0.5 to 2 cm, at least a series of 1 to 25 wells, preferably 2×25 wells, having a mean diameter of about 30 to 80 µm, preferably of about 40 to 60 µm, and with a very preferred diameter of about 50 µm, a depth of about 20 to 30 µm, preferably of 25 µm, said wells being spaced the ones of the others of about 60 to 120 µm. preferably, the wells have a sleek or rough wall, an ovale or round shape, with a flat or concave bottom.

Advantageously, the functionalized extremity may present a number of wells as elevated as possible. The number of wells may be such as the metallic guide is rigid enough for perforating the tissues or organs. In this embodiment, the mean diameter of the functionalized extremity may be of about 0.3 to 3.5 mm, preferably of about 0.35 mm. Advantageously, the metallic guide may be structured on a length of 0.5 to 2 cm, preferably of 1 cm, to form wells. Advantageously, the diameter of wells may be of about 30 to 80 µm, preferably of about 30 to 60 µm, for example 35 µm. Advantageously, the depth of the wells may be of about 20 to 30 µm, preferably of about 25 µm. The spacing of the wells may be of 20 to 120 µm, preferably 25 µm.

Advantageously, the functionalized end Ea may be in a cylindrical, plane, or spiral form or in a form modified so as to increase the well surface in contact with the fluids, the tissues and the cells.

According to a particular embodiment of the device according to the invention, said device further comprises a removable protective system at the functionalized extremity Ea.

According to a particular embodiment of the device according to the invention, said device further comprises a medical instrument possessing an internal opening in which said at least one metallic guide may slide.

By "metallic guide", it is meant for example a metallic butt full supple or a hollow rigid metallic butt, having a diameter from 0.2 to 3.5 mm and a length from $5\times10^{-2}$ to 2 m, and that may be inserted in a blood vessel, a little cavity or through an organ or a tissue, making it possible to be directed from the insertion site to the site of micro-analysis and/or micro-sampling in situ.

Particularly, a full flexible metallic butt may be constituted of an optical fibre, to an extremity Ea of which is associated a metallic ring supplied with at least one series of wells to which is directly coupled at least one reactive group specific of said substrate, said functionalized extremity Ea being perforating.

Advantageously, said metallic ring has a width of about 0.5 to 2 cm, and may presents at least a series of 1 to 25 wells, preferably 2×25 wells, having a mean diameter of about 30 to 80 µm, preferably of about 30 or 40 to 60 µm, and much preferably of about 50 µm or 35 µm, a depth of about 20 to 30 µm, preferably of 25 µm, said wells being spaced the ones of the others of about 20 to 120 µm, for example of about 60 to 120 µm. Preferably, the wells have a sleek or rough wall, an ovale or round shape, with a flat or concave bottom.

By "metallic guide", it is further meant a full or hollow, rigid or flexible butt, constituted of all or part of a metallic alloy, the features of flexibility, rigidity, oxidation and immunogenicity of which are consistent with such a use in the living being and particularly in the animal, and much particularly in human. Such biocompatible alloys may simply be identified by the man skilled in the art by means of his general knowledge and comprise notably the inoxidizable steels, the titanium-based alloys, the nickel, the cobalt, or mixtures of these ones.

The inventor have managed to demonstrate that a titanium and nickel alloy-based guide (Nitinol alloy) presents some particularly interesting properties in terms of general flexibility and rigidity at its extremity to be efficiently used in the endovascular or endocavitary pathways and also to efficiently perforate a tissue or an organ while minimizing the traumatism (the size of the perforation at the level of said tissue or organ is for example of the order of 0.05 to 0.5 $mm^2$, and preferably pf the order of 0.07 $mm^2$).

Advantageously, the metallic guide is a titanium and nickel alloy-based guide, preferably Nitinol-based (metallic guide sold by the Euroglex society).

Said metallic guide may be covered, except at the functionalized extremity Ea, with a hydrophilic polymer, preferably a hydrogel, or with a porous protective polymer layer, having a depth from about 0.1 to 51 µm. Advantageously, the protective polymer is constituted of a film of parylene, of $TiO_2$ or of OptoDex® (Arrayon Biotechnology, Switzerland), and more preferably of a film of parylene.

The removable protective system in which the metallic guide is inserted may take multiple forms, and notably the one of a flexible catheter, that may be determined simply by the man skilled in the art, for examples forms usable for the endovascular, endocavitary, transparietal, and notably transcutaneous pathway.

Said removable protective system may be inserted by endovascular pathway notably to reach the vessels of the heart, brain, lung, pancreas, kidney and liver.

Said removable protective system may be inserted by endocavitary accesses, notably by mean of an endoscope, by oral, anal, urogenital and respiratory pathway, or ENT by transmucosal pathway, or also by transcutaneous pathway by mean of a puncture at the level of the skin, to reach for example the mammary gland, and notably to the kidney, in an articulation, in the vertebral canal, by lumbar puncture or transparietally in the liver, the lung or the kidney, but also by transmucosal pathway, notably for the digestive tract.

The inventor has evidenced that the device according to the invention then allows to reach the tissues or organs, usually difficult to reach, by the endovascular, endocavitary or transparietal pathways, and notably transmucosal ou transcutaneous, usually used.

More generally, the inventor has evidenced that the device according to the invention allows, because of its specific features of general flexibility and of rigidity at its extremity, to reach and to perforate by transparietal (transcutaneous, transmucosal), endovascular or endocavitary pathway some organs and tissues being part of the digestive system from the oropharynx to the rectum (comprising the liver and the pancreas), of the urogenital system (comprising bladder, kidney, prostate, testis, ovary and mammary gland), of the tracheo-bronchial system (comprising lung), of the ENT system (comprising ear and rhinopharynx), of the osteo-articular (comprising synovial cavities), of the endocrine system, of neurocerebral system or the tegumentary system, then making possible the realization of diagnostic on pathologies that necessitated since then the realization of biopsies, nay, deep aggressive punctures as the transhepatic biopsies, comprising the sampling of cells by fine needle aspiration (also named FNA).

Advantageously, said removable protection system into which the metal guide is inserted is in the form of a flexible catheter adapted for endovascular or endocavitary delivery.

The device according to the invention is then particularly adapted for carrying out an investigation, for example in arteries and veins, heart vessels, the prostate, the mammary glands, the pancreas, the kidneys, the heart muscle, the central nervous system and the cavities or canals thereof, the brain or the liver.

According to a first particular embodiment of the device according to the invention, the removable protection system into which the metal guide is inserted is itself inserted into an endoscope. The device according to the invention is then particularly adapted for an endocavitary delivery.

The device according to the invention is then particularly adapted for carrying out an investigation for example, on the tracheo-bronchial system (among which the lungs), the digestive system from the pharynx to the rectum (including the liver and the pancreas), the uro-genital system (among which the bladder, the kidneys, the prostate, the testicles, the ovaries and the mammary glands), the ophthalmic system (lachrymal canals), of the otho-rhino-laringologic system (among which the ear and the nasopharynx), the osteo-articular system, or the central nervous system, more particularly through endo-spinal delivery or the mammary gland through endogalactophoric delivery.

According to a second particular embodiment of the device according to the invention, the metal guide composed of a fine transparietal aspiration needle and more particularly transcutaneous or transmucosal aspiration needle may be inserted into a removable protection system, for example a flexible catheter. The device according to the invention is then particularly adapted for a specific transcutaneous or transmucosal delivery.

The device according to the invention is then particularly adapted for carrying out an investigation, for example, as regards the teguments (the skin, the scalp, etc.), the breast, the kidneys, the lungs, the liver, the muscle, the osteo-muscular or osteo-articular system, the central or the peripheral nervous system or the endocrine glands (more particularly the thyroid, the parathyroid, the adrenal glands, the testicles, the mammary glands or the ovaries.

As regards the functionalized extremity Ea of the device according to the invention, it is provided with at least a series of wells to which are directly coupled reactive groups specific to a substrate to be tested.

"Specific reactive groups" means, for example, a nucleic acid sequence [DNA (amplifiat, fragment of a gene, EST, SNP) or NRA] complementary to a nucleic acid sequence to be detected, and an antigen specific to an antibody to be detected or an antibody or a fragment of antibody specific to an antigen to be detected, preferably an antibody or a fragment of antibody.

Advantageously, said specific reactive groups are positioned in the micro-wells of the functionalized extremity of the device according to the invention, according to an increasing or decreasing range. The man skilled in the art can determine simply, using their general knowledge and routine experiences, said range as a function of the affinity of the reactive group for the substrate. For example, the range of the reactive group is of the order of 50 to 500 µg/ml, preferably to 10 to 100 µg/ml, for a reagent, more particularly an antibody having an affinity for its substrate, more particularly an antigen of the order of $10^{-9}$.

"Antibody" preferably means an immunoglobulin of a living organism, a mammal, more particularly a human being and more preferably an IgG.

"Fragments of antibodies" means fragments of antibodies capable of maintaining a specific fixation of their antigens. The fragments Fab, Fab', F(ab')$_2$ or Fv can be cited as examples of such fragments of antibodies.

Methods for coupling reagents, more particularly proteins once on a metal support are well known to the man skilled in the art. Such methods, because of the low chemical reactivity of amino acids, generally require the activation of the metal surface either through oxidation mechanisms or by covering the latter with at least one layer of link molecules, most often of polymers (the latter may have for example thiol groups, carboxylic acids, and/or amines). As examples of such methods, the adsorption on metal supports of functional molecules organized in self-assembled monolayers (SAMs) and more particularly alcanethiols (refer to WITTSTOCK and SCHUHMANN, Anal. Chem., vol. 69, p: 5059-5066, 1997; and the international application WO 03/006948) or pyrrole (electrochemical polymerization of biotinylated pyrrole; DUPONT-FILLIARD and al., Anal. Chim. Acta., vol. 449, p: 45-50, 2001) can be mentioned.

Coupling antibodies or a fragment of the antibody to this layer of the functional molecules means a covalent link (like disulfide bridges between the free thiols groups of the alcanethiols) or non covalent link (like the streptavidine-biotin link between the biotin of a layer of polymer of the pyrrole/biotin complex and streptavidine of a streptavidine/antibody complex or antibody/streptavidine fragment).

According to a first preferred embodiment, the device according to the invention includes at least a metal guide, an Ea extremity of which is coupled to at least one reactive group preferably an antibody or a fragment of antibodies specific to a marker (antigen) of cancer, more particularly breast cancer, ovary cancer, prostatic cancer, cancer of the colon, intra-abdominal cancer, kidney cancer, liver cancer, lung cancer, pancreatic cancer, cancer of the central or peripheral nervous system or an endocrine gland (more particularly thyroid, the testicles or the ovaries).

As an example of a marker of breast cancer, marker CA 15-3 can be mentioned (Carcinoma-Associated Antigen 15-3; Duffy M. J., Shering S., Sherry F., McDermott E., O'Higgins N., Int. J. Biol. Markers, 2000 October-December; 15(4): 330-3), CA 27-29 (Carcinoma-Associated Antigen 27-29; Kaohsiung J., J. Med. Sci., 1999 September; 15(9): 520-8), CEA (Carcinoembryonic antigen; Soletormos G., Nielsen D., Schioler V., Mouridsen H., Dombernowsky P., Eur. J. Cancer, 2004 March; 40 (4): 481-6); TPA (Tissue Polypeptide Antigen); TPS (Tissue Polypeptide Specific Antigen; Given M., Scott M., Mc Grath J. P., Given H. F., Breast, 2000 October; 9 (5):277-80), HER2 (Fehm T., Jager W., Kramer S., Sohn C., Solomayer E., Wallwiener D., Gebauer G., Anticancer Research, 2004 May-June; 24 (3b): 1987-92), ER (Estrogene Receptor; Platet N., Cathiard A. M., Gleizes M., Garcia M., Crit. Rev. Oncol. Hematol., 2004 July; 51(1): 55-67), PR (Progesterone Receptor; Duffy M. J., Clin. Chem., 2005 March; 51(3): 494-503. Epub 2005 Jan. 6.), Ki-67 (cell proliferation-associated antigen of antibody Ki-67; Schlüter C., Duchrow M., Wohlenberg C., Becker M. H., Key G., Flad H. D., Gerdes J., J. Cell. Biol., 1993 November; 123(3): 513-22) and UPA (Urokinase Plasmogen Activator; Duffy M. J., Crit. Rev. Clin. Lab. Sci., 2001 June; 38(3): 225-62).

As an example of a marker of the ovary cancer, marker CA125 (Carcinom Antigen 125; Moss E. L., Hollingworth J., Reynolds T. M., J. Clin. Pathol., 2005 March; 58(3): 308-12), CA 15-3 and CEA (Valenzuela P., Mateos S., Tello E., Lopez-Bueno M. J., Garrido N., Gaspar M. J., Eur. J. Gyn. Oncol., 2003; 24(1): 60-2) can be mentioned.

As an example of a marker of the prostatic cancer, marker PSA (Prostate-Specific Antigen; Gray M. A., Clin. Lab., 2005; 51(3-4):127-33); PMSA (Prostate-Specific Membrane Antigen) and AR (Androgen Receptor; Birtle A. J., Freeman A., Masters J. R., Payne H. A., Harland S. J., BJU Int., 2005 August; 96(3): 303-7) can be mentioned.

As an example of a marker of the colon cancer, marker CEA (Duffy M. J., Clin. Chem., 2001 April; 47(4): 624-30), CA 19-9 (Carcinom Antigen 19-9), CA242 (Carcinom Antigen 242), CA 72-4 (Carcinom Antigen 72-4), TPA, TPS (Duffy M. J., van Dalen A., Haglund C., Hansson L., Klapdor R., Lamerz R., Nilsson O., Sturgeon C., Topolcan O., Eur. J. Cancer, 2003 April; 39 (6): 718-27) can be mentioned.

As an example of a marker of intra-abdominal cancer, marker CEA or CA 19-9 (Coban E., Samur M., Bozcuk H., Ozdogan M., Int. J. Biol. Markers, 2003 July-September; 18(3): 177-81) can be mentioned.

As an example of a marker of the cancer of pancreas, the marker TA90-IC (a 90-kDa immunogenic Tumor-associated Antigen), CA-19-9 (Chung M. H., Gupta R. K., Bilchik A J, Ye W, Yee R., Morton D. L., Curr. Surg., 2002 March-April; 59(2): 194-198), TPS, HCG beta (hCG beta, Human Chorionic Gonadotropin beta), CA 72-4, CEA, CA 19-9, CA 242 (Louhimo J., Alfthan H., Stenman U. H., Haglund C., Oncology, 2004; 66(2): 126-31) can be mentioned.

As an example of a marker of the liver cancer, the alpha-fetoprotein marker can be mentioned.

As an example of a marker of lung cancer, the marker Cyfra A41 (Cytokeratin fragment 41), SCC (Squamous Cell Carcinoma antigen), ACE (Angiotensin Converting Enzyme), CA 19-9, CA 125, NSE (Neuron Specific Enolase), chromogranine A, CYFRA 21-1 (Cytokeratin fragment 21-1,) CA 15-3 can be mentioned.

According to a second preferred embodiment, the device according to the invention includes at least one metal guide whose an Ea extremity is coupled to at least one reagent, preferably an antibody or a fragment of an antibody, specific to a specific marker of an inflammation, more particularly rheumatoid arthritis.

As an example of a marker of rheumatoid arthritis, IL-1β, IL-1Rα, IL-2, IL-2R, IL-4, IL-5, IL-6, IL7, IL8, IL10, IL12p40P70, IL-13, IL-15, IL-17, le TNFα, IFNα, IFNγ, le GM-CSF, le MIP-1, IP-10, the MIG, Eotaxine, the RANTES and the MCP-1 (COCKRUM and al., Lab Automation, BTi, October 2005, p: 19-21) can be more particularly mentioned.

According to a third preferred embodiment, the device according to the invention comprises at least one metal guide, an Ea extremity of which is coupled to at least one reagent preferably an antibody or a fragment of an antibody, preferably specific to a specific marker of an infection, more particularly a viral, bacterial or parasitic infection.

Many infectious markers are known to the man skilled in the art and this can identify very easily the specific marker or markers associated to a given infection.

According to a fourth preferred embodiment, the device according to the invention includes at least one metal guide, an Ea extremity of which is coupled to at least a reagent, preferably an antibody or a fragment of an antibody, specific to a specific marker of the graft rejection.

Numerous markers of a graft rejection are known to the man skilled in the art. As an example, MIP-1β and the VE-cadherine for heart transplantations (ROUSSOULIÈRES and al., Circulation, vol. 111(20), p: 2636-2644, 2005) can be mentioned.

As regards the specific markers which have been described above, the man skilled in the art will be able to use their general knowledge and to easily identify, without any excessive experiment, the antibodies or specific fragments of antibodies which can be used in the device according to the invention. As an example of such antibodies, the antibodies available at TEBU or AXXORA can be mentioned. The man skilled in the art can also obtain such antibodies using well-known immunization methods.

Similarly, the man skilled in the art will be able to identify adapted specific nucleic acids which can be used in the device according to the invention.

According to a fifth preferred embodiment, the device according to the invention includes at least one metal guide, an Ea extremity of which is coupled to at least one reagent, preferably an antibody or a fragment of an antibody, which is specific to a specific marker or a set of specific markers of neurodegenerative pathologies, such as for example Alzheimer's disease (MA), Parkinson's syndrome, amyotrophic lateral sclerosis (SLA), with this list not being exhaustive.

Several markers are known and used by the man skilled in the art for studying such pathologies. As an example for insane or pre-insane conditions, total protein Tau (MAPT-Microtubule Associated Protein Tau), amyloid peptide ABETA1-42, hyperphosphorylated protein Tau (p. Tau phosphorylated in 128), described for example by Waldemar G., Dubois B., Emre M. and al, Eur. J. Neurol., 2007, 14, pp 1-26; Dubois B., Feldmann H. H., Jacova C., Dekosky S. T. and al, Lancet Neurol. 2007, 6, pp 734-746; Krolak-Salmon P. and al. "Vers un diagnostique biologique de la maladie d'Alzheimer et des syndromes apparentés", La Revue de médecine interne (2008), doi:10.1016/J. revmed. 2008 Jan. 29. These markers can be determined by a technique Antigen-Antibody of the ELISA.INNOTEST B-Amyloïd type (1-42), INNOTEST hTAUAg, INNOTEST PHOSPHOTAU (181p); Innogenetics, Ghent, Belgium.

Other markers also make it possible to test the deteriorated condition of the brain and more particularly Visinin-like protein (VLP6 or VILIP-1 or VSNL), as described for example by Ref: Lee J. M. et al, Clin. Chem., 2008, 54, pp 1617-1623. These markers can be used while implementing the present invention.

As regards Parkinson disease and multi-systematised (synucleopathies) atrophies, marker Alpha-SYNUCLEINE (Mollenhauer B., Cullen V., Khan I., Experimental Neurology, 2008, 213, pp 315-325) can be mentioned.

Finally, markers which are non specific to affections concerning the central nervous system (SNC) exist, which can be used within the scope of the present invention. These are proteins originating from SNC such as protein GFAP, myelin, neuropeptides and neurotransmitters. Protein BNDF (brain derived neurotrophic factor), more particularly described in the document by the University of California, San Diego, Medicine & health/diseases February 2009, is also of particular interest. Besides, immune response proteins, for example IgG, albumin, complement protein, reactive protein C, as well as inflammation protein, such as for example, Transferrin, Haptoglobine, Ceruloplasmine, Lysozyme, Enolase can be used when implementing the invention.

Whatever the embodiment of the invention, several different markers, i.e. markers of various pathologies, can be placed in wells of the same metal guide. Then, markers can be placed in the wells so that the various markers do not interact with each other.

Advantageously, the device according to the invention or at least in its functionalized terminal part in contact with the substrate to be analyzed shows a level of assurance of sterility (SAL for Sterility Assurance Level) of the order of $10^{-6}$. Various alternative solutions can be considered so as to reach this level of sterility. A possibility consists in sterilizing a device in the absence of the reactive groups specific to the substrate to be detected, and then in adding the latter under sterile conditions. Another possibility consists in sterilizing the device after adding reactive groups, which requires the use of sterilization techniques which do not significantly reduce the activity of said reactive groups (for example sterilization using ethylene oxide or radiation).

A second object of the invention is an ex-vivo detection method for a substrate existing in a tissue or an organ, characterised in that it includes the following steps:

a) incubation of the functionalized Ea extremity of a device according to the invention with a solution comprising at least one detection agent specific to said substrate, when said extremity is in contact with said tissue or organ to be examined.

b) detection of said substrate.

The step of incubation is performed during a time sufficient so that the detection agent in the solution, more particularly an antibody, can specifically get fixed to the substrate (marker, antigen, antibody, etc.), more particularly an antigen and optionally existing at the end of the device. The man skilled in the art can easily determine, using their general knowledge and routine experiment, this incubation time as a function of the affinity of the detection agent in solution, more particularly an antibody for its substrate, more particularly an antigen. This incubation time also depends on the temperature of the solution during the incubation. As an example, the incubation time is of the order of 1 minute to 2 hours, preferably 5 minutes to 1 hour and particularly preferably from 10 to 30 minutes for a temperature between 20° C. (room temperature) and 37° C.

Advantageously, the detection agent in solution is different from the specific reagent coupled to the functionalized extremity of the device according to the invention.

Preferably, the detection agent is an antibody.

Advantageously, the antibody in solution and the antibody coupled to the functionalized extremity of the device according to the invention are each a polyclonal antibody preferably said antibodies are identical.

Advantageously, the antibody in solution and the antibody coupled to the functionalized extremity of the device according to the invention are each a monoclonal antibody preferably said antibodies are different.

Advantageously, the antibody in solution is marked and more particularly, it is coupled to an enzyme, for example peroxidase or phosphatase alkaline.

According to a first particular embodiment of the method according to the invention, the method further includes a step a') of incubation of said extremity in a solution comprising at least one detection agent specific to the detection agent of step a) interposed between steps a) and b).

The man skilled in the art can simply identify using their general knowledge, the antibodies adapted to the method according to the invention. As an example, it is possible to use in this second step, an antibody specifically recognizing mouse immunoglobulins if such mouse immunoglobulin specifically directed against the substrate (marker, antigen, antibody, etc.) to be identified are used at step a).

According to a second particular embodiment of the method according to the invention, the method according to the invention includes a step of washing, following the step of incubation a) and possibly step a') which washing step makes it possible to eliminate antibodies which are not specifically fixed to a marker (the antigen).

The protocol of such a washing step also belongs to general knowledge and can be simply determined by routine experiments. As an example, such a step is performed with a solution including a more or less important concentration of detergent (0.05 to 1%) such as TRITON X100® or the TWEEN 20®, as a function of the affinity of the antibody in solution for its specific antigen.

The step of detection is carried out by evidencing an activity, more particularly an enzymatic activity coupled to the antibody used in step a) or optionally step a').

The protocol used for this step of detection depends on the marker used and more particularly the enzyme used, for example peroxidase and alkaline phosphatase, and belongs to the general knowledge of the man skilled in the art.

This detection step makes it possible to deduce the quantity of specific substrate (for example of antigen) fixed to the functionalized extremity of the device and finally the quantity of the specific substrate existing at the level of the organ or of the tissue where the micro-analysis and/or micro-sampling was carried out.

Finally, the various reactive groups which can be used for carrying out the method according to the invention are well known to the man skilled in the art and more particularly include the reagents used for the immuno-enzymatic or immuno-fluorescence dosage technique, for example on a solid support [ELISA technique, protein chips (ESPINA and al., mentioned above, 2004)].

A third object of the invention consists in using a device according to the invention for manufacturing a tool intended for diagnosing cancer, an inflammation, an infection, a graft rejection or a neurodegenerative pathology in a patient.

According to a particular embodiment of the invention, said diagnostic tool may include at least a metal guide inserted into a flexible catheter inserted into an endoscope.

According to another particular embodiment of the invention, said diagnostic tool may include at least one metal guide consisting into a transparietal aspiration needle and more particularly transcutaneous or transmucosal aspiration which can be inserted into a removable protection system for example a flexible catheter. In addition, the removable protection system and the metal guide cooperate so as to enable the contact of the functionalized Ea extremity of said guide with the micro-analysis or and/or micro-sampling site.

In these two particular embodiments of the invention, said at least one metal guide may be associated with at least a part of the length of an optical fiber with a view to identification and positioning.

Advantageously, said diagnosing instrument is delivered by endocavitary route.

Said tool thus makes it possible to carry out a microanalysis and/or a micro-sampling in the digestive system from the pharynx to the rectum (including the liver and the pancreas), of the uro-genital system (including the bladder, the urether, kidney, prostate), tracheo-bronchial system (including the lungs), the ORL system (including the ear and the nasopharynx), and the osteo-articular system (including synovial cavities).

Preferably, said diagnostic tool is delivered by a transparietal route, more particularly by transmucosal or transcutaneous route.

Such a diagnostic tool also makes it possible to analyze tissues or organs which can hardly be reached through the endocavitary or endovascular routes usually used. Such a diagnostic tool also makes it possible to carry out a microanalysis and/or micro-sampling using the transparietal route at the level of the skin, the testicles, the prostate, the ovaries, the mammary glands and also the kidney and the liver, the peripheral nervous system as well as the central nervous system, more particularly by endo-spinal route as well as the endocrine system (for example thyroid).

Examples hereinunder make it possible to illustrate the invention and are given as non-limitative examples.

DETAILED DESCRIPTION OF THE INVENTION

The figures are illustrations of the sensitivity and specificity of the method used.

EXAMPLE 1

Preparation of a Nitinol-Based Metal Guide and the Activation Thereof

Figure 1:
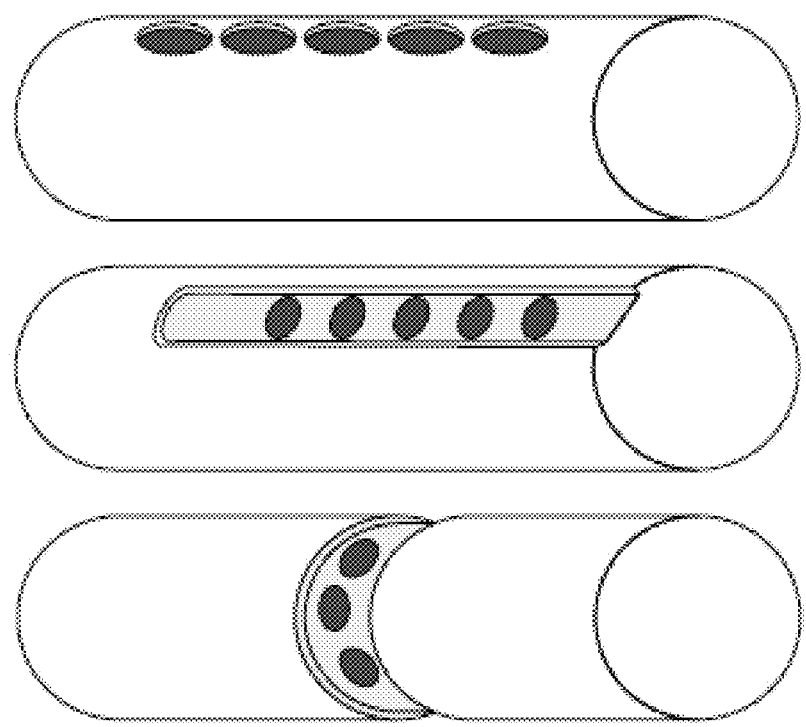
FIG. 1 shows various possibilities for structuring metal guides.

The surface of a Nitinol-based metal guide (Euroflex) is structured for defining locations, for example wells, where the reactive groups will be placed and where the biochemical interactions will occur (FIG. 1).

Said "wells" can be obtained using various methods such as, for example focus ion beams lithography (FIB, Xie and al, Nuclear Instruments & Methods in Physics research Section B-beam Interactions with Materials and Atoms, 211(3): 363-368, 2003), by a laser lithography followed by an electrochemical etching and a laser ablation.

Figure 2:
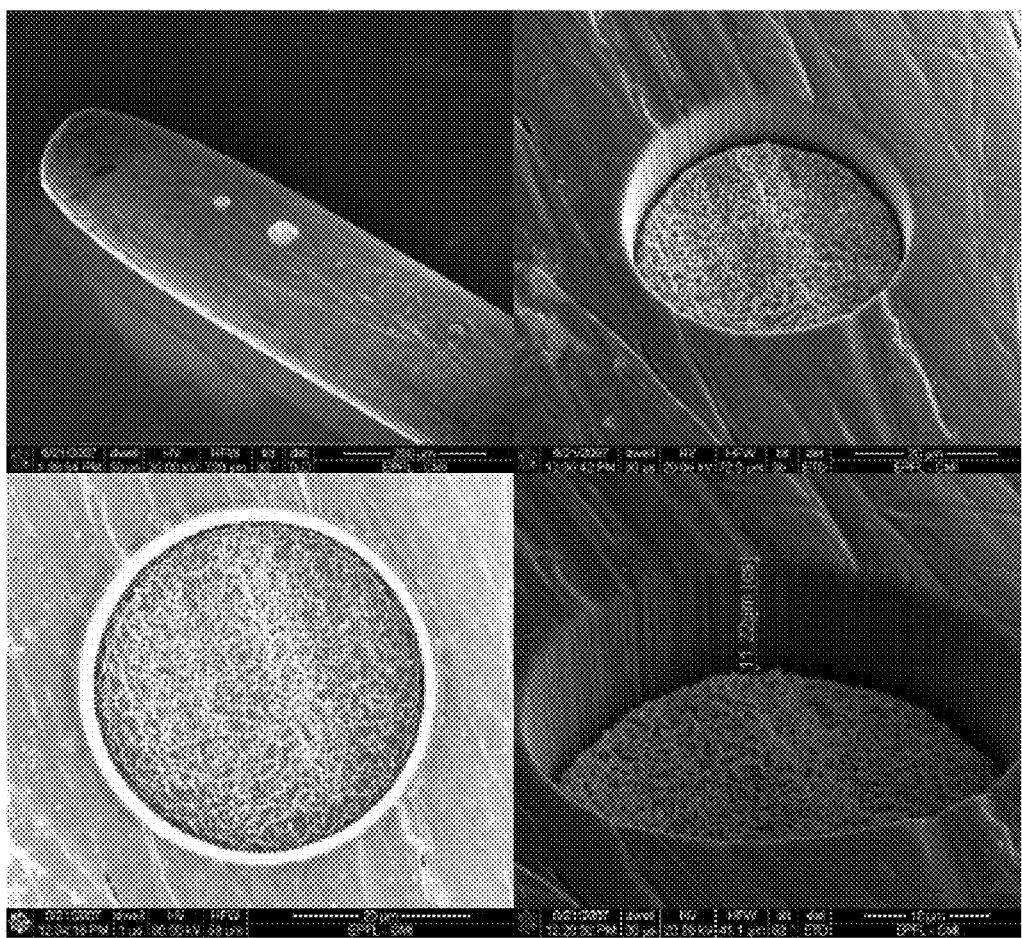
FIG. 2 shows scanning electronic microscopy photography of various holes made by FIB (important surface roughness resulting from etching non-homogeneity can be observed).
Figure 3:
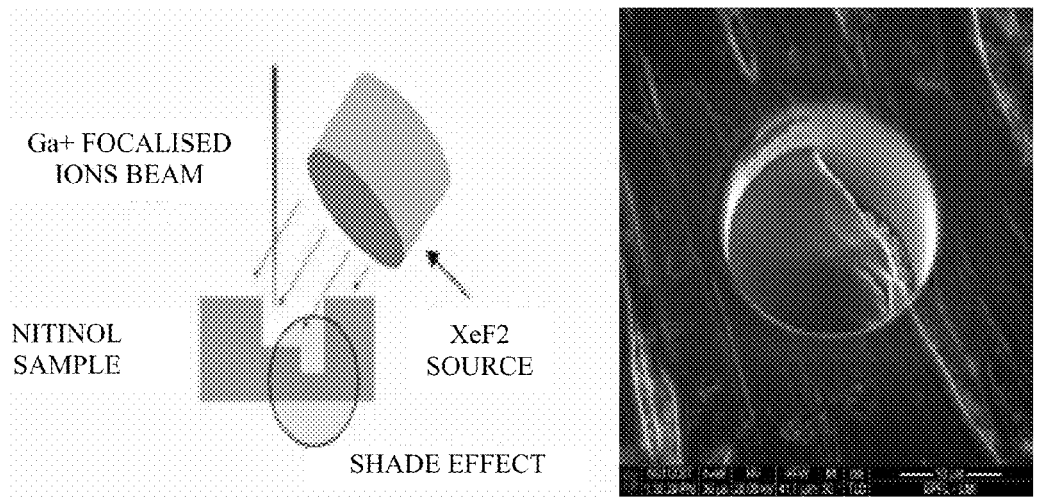
FIG. 3 shows an explanation and an observation of the shadowing effect of the milling technique assisted by fluorine.

Using the FIB technique, the machine creates an ion beam which is focused onto the surface which must be structured. Under the mechanical action of the ion beams, the atoms of the surface material are eliminated from the surface. Holes having a diameter of 20 μm can be formed with the technique FIB in a reasonable time with an etching reader of 8 $\mu m^3\ s^{-1}$ in a beam current of 20 nA. FIG. 2 shows holes having a diameter of 5, 20 and 40 μm with a depth of 10 and 20 μm. The surface of the bottom of the hole is rough because of the re-deposition of the pulverized material during the etching. The etching rate has been measured at 200 nm $min^{-1}$ on a circular area, 40 μm in diameter and a beam current of 20 nA. This results in an etching rate 0.2 $\mu m^3\ nC^{-1}$ (approximately 5 $\mu m^3\ s^{-1}$) which corresponds to a processing time of 20 minutes to make a hole 20 μm in diameter and 20 μm in depth. In order to improve the surface roughness, a fluorine ($XeF_2$) assisted milling technique was used; a very low surface roughness was then obtained but as the $XeF_2$ was not exactly along the axis of the etching beam, a shadowing effect was noted (FIG. 3).

Figure 4:
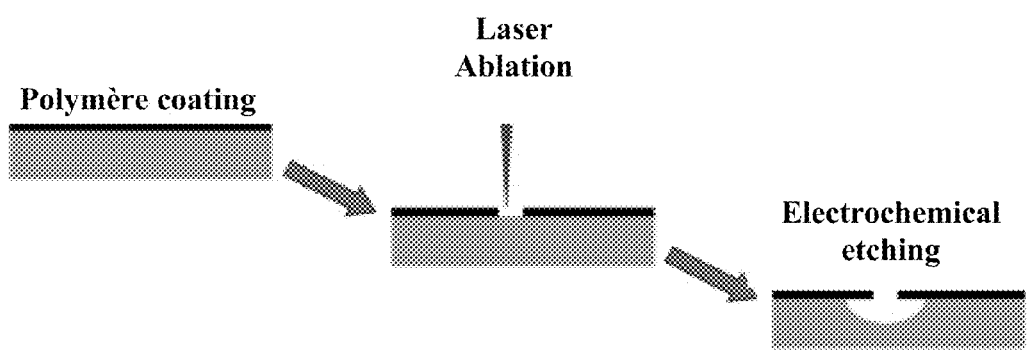
FIG. 4 shows the advance of micro-shaping operations.
Figure 5:
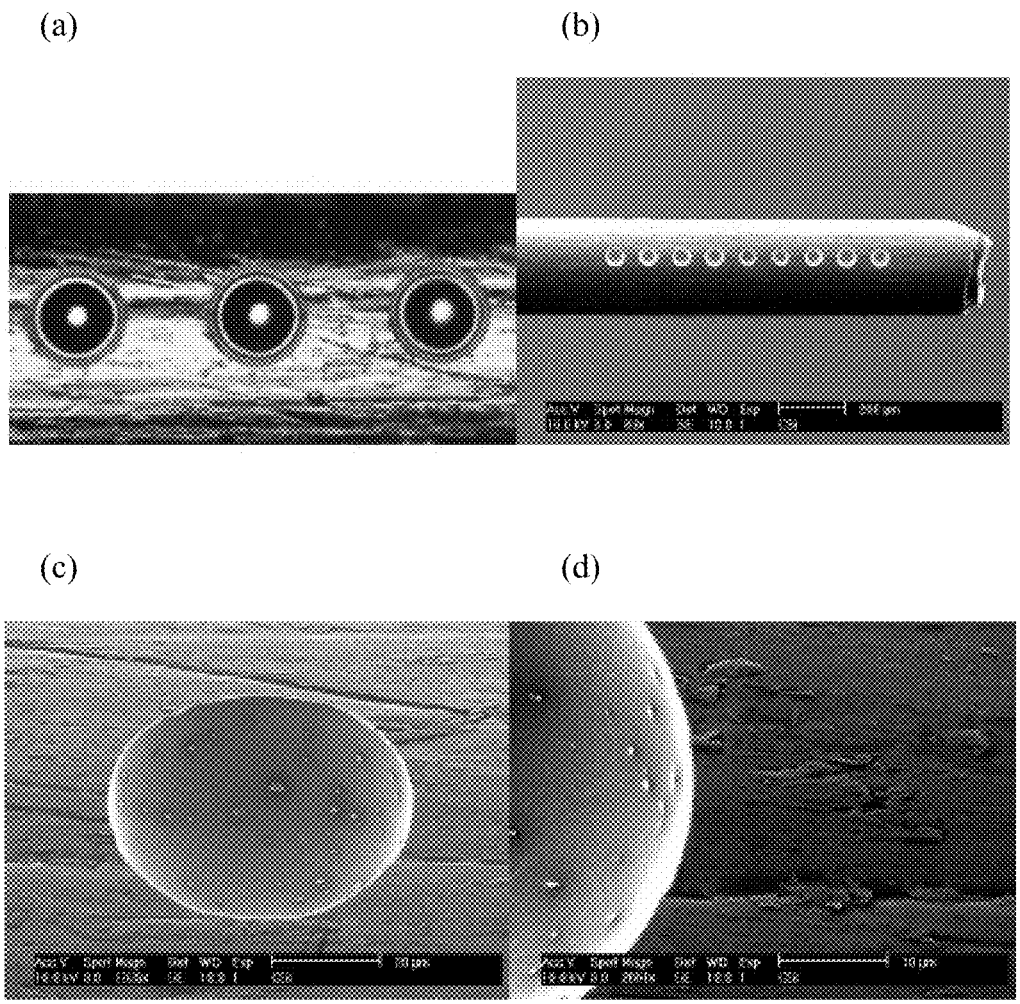
FIG. 5 shows (a) hemispheric holes observed by optical microscope (b) series of holes observed on a guide using Nitinol by scanning electronic microscopy (c) a detail of a cavity (d) comparison of the surface roughness in the cavity with the surface roughness of the guide.

The laser lithography technique and electrochemical etching consist in a first step of coating the surface with a layer of polymer. In a second step, the polymer layer is machined using the laser ablation. In a third step, the surface is etched using an isotropic electrochemical etching through the opening provided in the polymer layer (FIG. 4). FIG. 5 shows the result of various structuring tests on Nitinol based metal guides.

Figure 6:
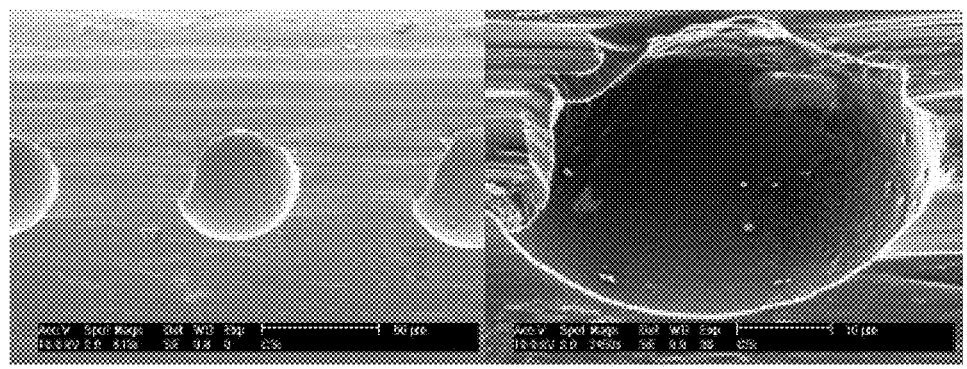
FIG. 6 shows pictures of scanning electronic microscopy showing the same hemispheric hole as in FIG. 5 after the electrochemical polishing treatment.

In addition, Nitinol based metal guides which are used in vivo are usually processed through an electrochemical polishing which replaces the native NiTi oxide layer with a biocompatible $TiO_2$ layer. The machined guides having holes have to undergo this method in order to estimate the influence of the method on the structure of the holes (FIG. 6).

Another way to prepare cavities on the surfaces of the Nitinol based guides uses laser ablation. The utilization of short laser impulsion enables the local evaporation of metal without affecting the surrounding metal because of the heat generated. The smallest reported dimensions are of the order of 20 μm.

If the three methods mentioned hereabove make it possible to create wells, the electrochemical etching method gives the best results.

EXAMPLE 2

Trauma Consecutive to the in vivo Insertion of a Metal Guide Into a Particular Organ For these experiments, metal micro-guides (MTI 0.012" Silver speed) were used and said metal guides were inserted into micro-catheters.

The device was introduced in pigs under general anesthesia at the level of an aspiration, then at the level of the scarpa up to the kidney through the endovascular route (via the femoral artery). This guide was provided by the follow-up of said device in the femoral artery through an arteriography.

When the device is positioned at the entrance of the kidney, it is introduced into the kidney by endo-arterial invasion. This penetration into the tissue was a few millimeters deep and said device was kept there for about ten minutes.

Finally, the device was removed.

Animals were euthanized and their kidneys were sampled to estimate their conditions after the penetration of the device according to the invention.

The result showed that no important hemorrhage in the kidney was associated to the invasion. The most important damage noted showed a dimension of 3×1 mm at the level of the invasion site.

The device according to the invention thus makes it possible to have access to an organ while being very slightly invasive.

EXAMPLE 3

Micro Trauma Following the Insertion of a Device Into the Liver

Metal micro-guides (MTI 0.012" Silver speed) were used which metal micro-guides were placed in a fiberscope which is different from example 1.

The device was introduced into pigs under general anesthesia at the level of an aspiration, at the level of the scarpa then up to the liver through endo-arterial navigation (via the femoral artery). This guiding was provided by a control of said device in the femoral artery through arteriography.

When positioned close to the liver, the device was introduced into this organ. This penetration into the tissue was a few millimeters deep and said device was kept there again for approximately ten minutes.

Finally, the device was removed.

As before, the liver sampling of the operation made it possible to estimate the aggressivity of the operation on the organ.

No macroscopically visible damage could be seen at the surface of the liver. When cut, the presence of two intra-parenchymatous hemorrhagic nodes of the sub-capsular seat 1.5×0.4 cm and 1.8×0.5 cm in dimension could be seen. Histologically, the hepatic architecture is kept in every aspect with a congestion of sinusoids, portal venules and centro-lobular veins without any other remarkable anomaly.

CONCLUSION

The results showed that hemorrhagic lesions were minimum: two minor microscopic damage could be seen without any destruction of parenchymatous cells and with a simple congestion of capillaries and centro-lobular veins.

The utilization of a metal guide thus makes it possible to obtain a minor trauma and, in any case, largely smaller than that resulting from a biopsy.

EXAMPLE 4

Figure 7:
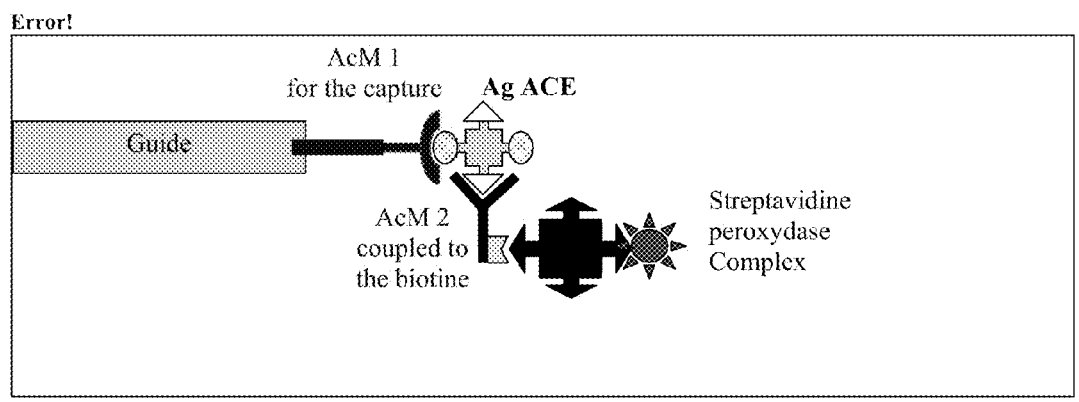
FIG. 7 shows a diagram of the device of the invention for the immuno-capture with a first monoclonal antibody (AcM 1) and the revelation of the antigen ACE with a second monoclonal antibody (AcM 2).

Study of the Parametres for the Conception and Production of a Device Enabling in vitro Immunocapture and Detection of Antigen Ace on Solid Supports The device uses the principle of the ELISA technique making it possible to show antigen ACE. Two monoclonal antibodies recognizing different epitopes on this antigen were used for the capture (AcM1) and revelation of the antigen ACE (AcM2). These monoclonal antibodies having the same isotope (IgG1) the revelation of the ACE antigen was made using a monoclonal antibody coupled to biotin and a streptavidine-peroxidase complex (FIG. 7).

Two types of support were used, either plates for ELISA or rigid plastic butts.

Plates for ELISA (Greiger)

100 µl of a monoclonal antibody directed against the antigen ACE (clone 5910 or clone 5905, produced in mice and marketed by Medix Biochemical) diluted (1/5000 and 1/128000) in carbonate/bicarbonate buffer were placed in each well, and the plate was placed for 1 hour at 37° C. One negative control was obtained by replacing the antibody by carbonate/bicarbonate control solution.

After three washings with 250 µl of PBS per well, the free sites of the plate have been saturated with 200 ml of 3% PBS-BSA (bovine serum albumin) for 2 hours at 37° C.

Then the wells were washed three times with 250 µl of 0.5% PBS-Tween prior to adding 100 µl per well of an antigen ACE positive serum diluted within 1/10, 1/100, 1/1,000 with PBS-Tween and the plate was incubated for 1 hour at 37° C.

Three washings with 250 µl with PBS-Tween per well were carried out prior to adding 100 µl per well of a monoclonal antibody directed against antigen ACE (clone 5909 produced in mice and marketed by Medix Biochemical, which is different from the previous capture antibodies used because of its constant affinity and the recognized epitopes) biotynylated within 1/500 with PBS-Tween and the plate was incubated again for 1 hour at 37° C.

After three washings using PBS-Tween, 100 µl of streptavidine complex coupled to peroxidase diluted within 1/2000 were added in each well and incubated for 1 hour at 37° C.

After three washings with PBS-Tween, the revelation was carried out by adding 200 µl per well of the substrate ($H_2O_2$) and chromogen (OPD, Sigma) mixture in a citrate-phosphate control (pH 5).

In parallel, the same operation was carried out using a "normal" patient serum as an antigen (negative control with an ACE dosage of <5 UI/ml).

The reaction was then stopped by the addition of 50 µl of 1M sulfuric acid per well. The absorbance was read at 492 nm on a plate reader (ref: ELX. 800 UV).

Figure 8:
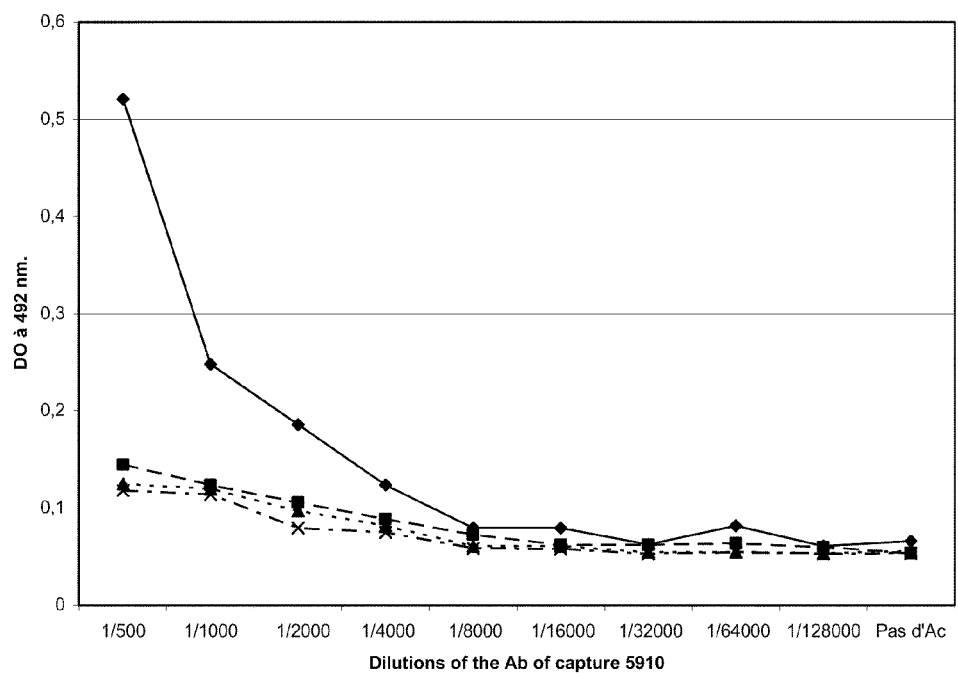
FIG. 8 shows the results of ELISA with the capture antibody 5910 and the revelation with antibody 5909 (absorbance obtained with an antigen ACE positive serum).
Figure 9:
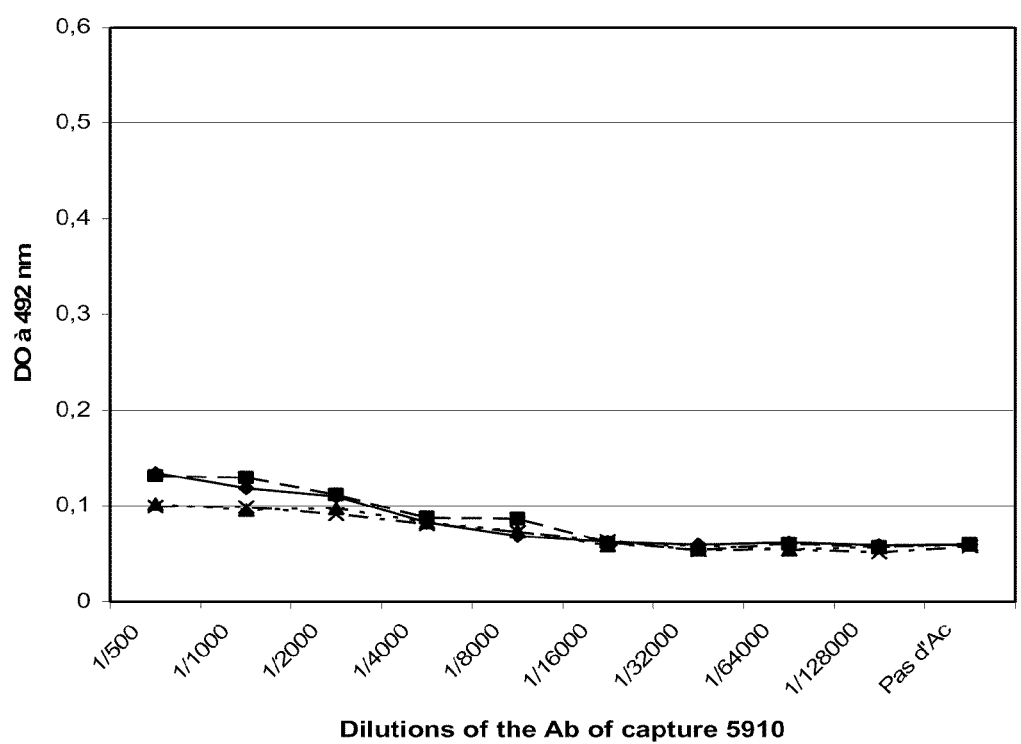
FIG. 9 shows the results of ELISA with the capture antibody 5910 and the revelation with 5909 antigen (absorbance obtained with a antigen ACE negative serum).

The results obtained by using the monoclonal antibody 5910 for immuno-capture (diluted within 1/500 then half by half up to 1/128000) and the revelation through the biotinylated monoclonal antibody 5909 are shown in FIG. 8 for the antigen ACE positive serum, and in FIG. 9 for the antigen ACE negative serum.

Figure 10:
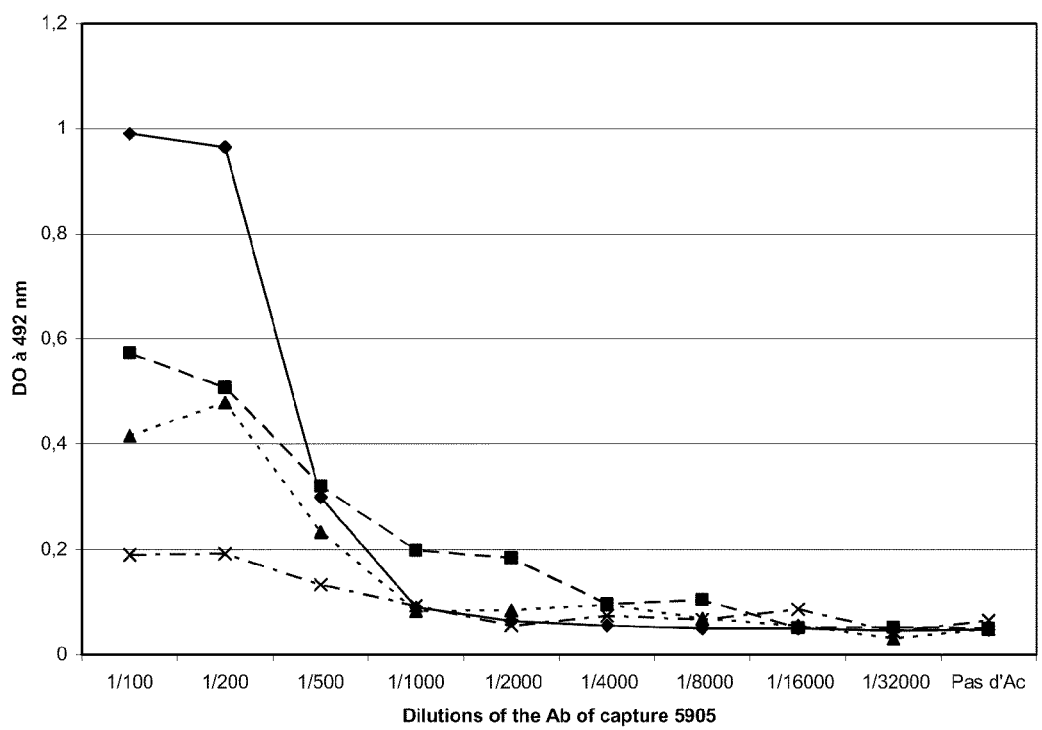
FIG. 10 shows the results of ELISA with the capture antibody 5905 and the revelation with the antibody 5909 (absorbance obtained with an antigen ACE positive serum).
Figure 11:
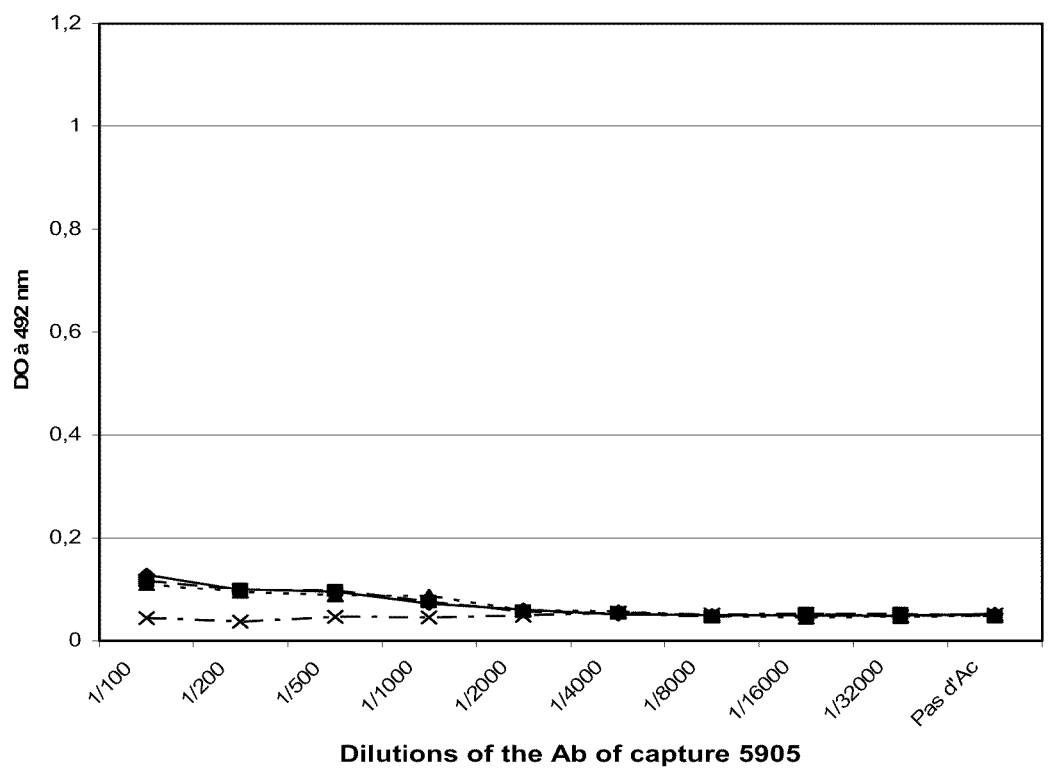
FIG. 11 shows the results of ELISA with the capture antibody 5905 and the revelation with the antibody 5909 (absorbance obtained with an antigen ACE negative serum).

The results obtained using the monoclonal antibody 5905 for immuno-capture (diluted within 1/100, 1/200, 1/500 then half by half up to 1/32000) and the revelation using the biotinylated monoclonal antibody 5909 are shown in FIG. 10 for the antigen ACE positive serum and in FIG. 11 for the antigen ACE negative serum.

Captions of FIGS. 8 to 11:
Ordinate: absorbance (DO) at 492 nm
Abscissa: dilutions of capture antibodies (5910 or 5905)
♦ ACE positive serum dilution within 1/10
■ ACE positive serum dilution within 1/100
Δ ACE positive serum dilution within 1/1000
x=no serum The results show that the antigen ACE positive serum within 1/10 gives an absorbance (DO) above 0.5 when the capture monoclonal antibodies used within 1/500 (FIG. 8). Under the same conditions, the antigen ACE negative serum gives a DO of less than 0.15 (FIG. 9).

It should however be noted that better results were obtained with the capture monoclonal antibody 5905 and detection monoclonal antibody 5909 couple (FIGS. 10 and 11) than with the capture monoclonal antibody 5910 and detection monoclonal antibody 5909 couple (FIGS. 8 and 9). As a matter of fact, a DO of 1 was noted with the antigen ACE positive serum diluted within 1/10 (FIG. 10) whereas the antigen ACE negative serum gives a DO of 0.1 (FIG. 11) under the same conditions. These results were confirmed using a capture monoclonal antibody 5910 in various dilutions (data not shown).

Rigid Classic Supports

In a first step, rigid plastic supports in the form of butts 2 to 3 cm in length and 0.5 to 1 mm in diameter were activated.

In a second step, the thus activated supports were placed in 1 ml haemolyse micro-tubes (Fisher) and were functionalized with a monoclonal antibody directed against the antigen ACE (clone 5910 produced in mice and commercialised by Medix biochemical) and diluted within 1/50, 1/100, 1/250, 1/500 in a carbonate/bicarbonate (250 µl/tube) control for 1 hour at 37° C. A negative control was made by replacing a monoclonal antibody with a carbonate/bicarbonate control. After a fixation and washings, saturation was obtained with 500 µl of 3% PBS-BSA overnight with a temperature of +4° C.

Then the supports were incubated with 250 µl of antigen ACE positive serum diluted within 1/10, 1/100 with PBS or with serum from a "healthy" subject (antigen ACE negative control) with the same dilution for 1 hour at 37° C.

A monoclonal antibody directed against the antigen ACE (clone 5909 produced in mice and marketed by Medix Biochemical, which is different from the purified clone 5910 by its constant affinity and by the acknowledged epitopes) within 1 mg/ml was dialysed overnight at 4° C. against a 0.1 M borate control, pH 8.8. A 10 mg/ml DMSO biotin solution was then added in 50 µg/mg of antibodies. After an incubation of 4 hours at room temperature and under stirring, 1 M ammonium chloride was added, in a quantity of 20 µl/250 µg of biotin and the obtained solution was incubated again for 1 minute at room temperature. Upon the stopping of the reaction, the marked antibody was dialysed for 24 hours at +4° C. against PBS and this marked antibody was kept as aliquots at −20° C.

After 3 washings with PBS-Tween, the supports were incubated with 250 µl of biotinylated antibody 5909 and diluted within 1/500 with PBS-Tween for 1 hour at 37° C.

Detection of biotin (ester of 6-biotinamidocaproylamidocaproic acid and N-hydroxysuccinimide, Sigma) was evidenced using a steptavidine-peroxidase complex (Amersham Biosciences) diluted within 1/2000 in PBS for 1 hour at 37° C.

The revelation of enzymatic activity was carried out by adding 750 µl of the substrate ($H_2O_2$) and chromogen (OPD, Sigma) mixture per tube in a citrate-phosphate control (pH 5).

Figure 12:
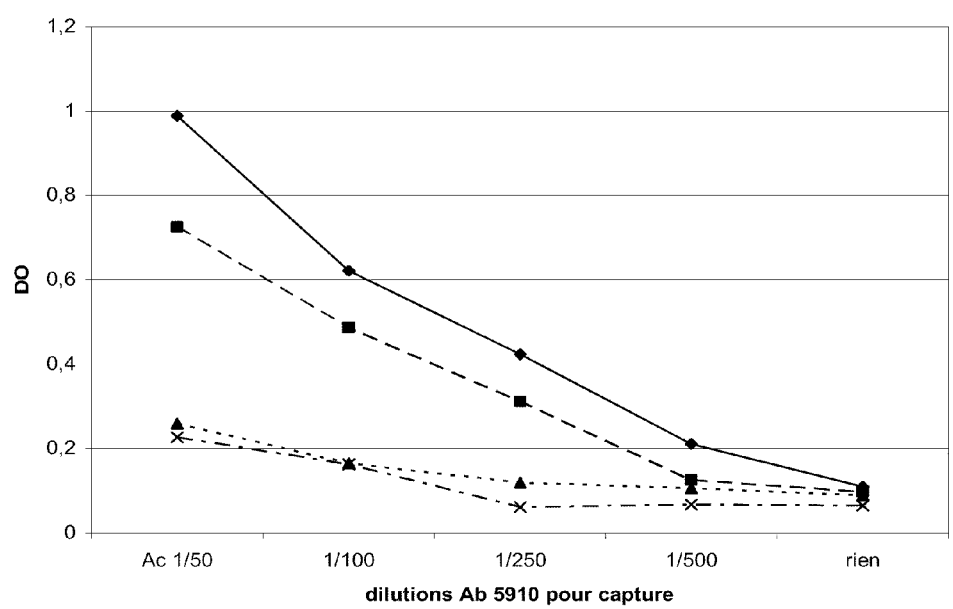
FIG. 12 shows the results of ELISA with the rigid plastic butts with capture antibody 5910 and the revelation with antibody 5909 (absorbance obtained with a positive antigen ACE serum).

The reaction was then stopped by adding 1M sulfuric acid.
Absorbance was read at 492 nm.
ELISA results on plastic butts are shown in FIG. 12.
Captions of FIG. 12:
Ordinate: absorbance (DO) at 492 nm
Abscissa: dilution of capture antibody 5910
♦ antigen ACE dilution within 1/10
■ antigen ACE dilution within 1/100
Δ negative control dilution within 1/10
x negative control dilution within 1/100

In general, the results show that DOs are 7 to 10 times higher with antigen ACE positive serum than those obtained with antigen ACE negative serum.

The best results were obtained with rigid plastic supports on which capture monoclonal antibody 5910 diluted within 1/50 or 1/100 was fixed.

The best Antigen ACE concentration detected corresponds to the patient's serum diluted within 1/100, i.e. 6 UI/ml (close to the rate considered as "normal": <5 UI/ml) and when the dilution of the detection of monoclonal antibody 5909 is within 1/500.

Using plastic supports makes it possible to validate the specificity and sensitivity of immuno-capture processes on functionalised metal butts according to the above-mentioned protocol.

CONCLUSION

The good results obtained for the detection of antigen ACE with the in vitro immuno-capture and revelation techniques validate the evaluation of "functionalized butt" devices making it possible to capture in vivo the antigen ACE followed by the ex vivo revelation.

EXAMPLE 5

Identification of the Expression of the Marker Ace in a Breast Tumor for Example Under the Control of Imaging Techniques and More Particularly Radiological Techniques According to the protocol described in the application PCT WO 03/006948, in a first step, an alcanethiol layer is absorbed on one of the ends of Nitinol-based metal guides (Euroflex), in a first step. In a second step, the free thiol functions of this layer make it possible to form disulfide bridges with a monoclonal antibody directed against the antigen ACE.

The metallic guide obtained is then introduced into a biopsy needle adapted to be used in an animal or a human being.

An extemporaneous anatomo-pathological examination is performed using this device on a tumor to be operated (mammary tumour) after it has been removed from a patient suffering breast cancer. According to an alternative solution, when the medical ethic conditions are present, the micro-incision is performed in the breast under a local or general anaesthesia in a patient suffering from breast cancer. The needle in which the metal guide coupled to the antibody directed against the antigen ACE is inserted, is introduced into the tumour or through the micro-incision then guided up to the tumour while following the progression thereof by imaging, and more particularly echographia.

Said micro-invasive guiding system then makes it possible to take out the end of the metal guide coupled to the antibody directed against the antigen ACE. The end of the metal guide is then introduced into the tumour (by perforation) at a depth of the order of a few millimeters. After a short waiting time, of the order of ten minutes, which enables the immuno-capture by the antigen ACE optionally expressed by the tumour, the device is removed.

The micro-sampling is limited to an in vivo immuno-capture of the analyte and does not request any biopsy.

Finally, the device is removed, then an ELISA dosage of the marker ACE is carried out on the end of the device with a monoclonal antibody directed against the marker ACE which is differentiated from the capture antibody by its constant affinity as regards the antigen ACE and by the recognised epitopes, and which is coupled to biotin.

The revelation of the enzymatic activity using a streptavidine-peroxidase complex makes it possible to deduce the expression of the marker ACE by the tumour and to modulate the therapy to be used to treat a patient at best accordingly.

EXAMPLE 6

Skin Cancer

According to the protocol described in the application PCT WO 03/006948, a layer of alcanethiol has been absorbed on the end of a Nitinol-based metal guide (Euroflex) in a first step. In a second step, free thiol functions of this layer enable the formation of disulfide bridges with a monoclonal antibody directed against FAP marker (Fibroblast-activation protein; RETTIG et al., Proc. Natl. Acad. Sci. USA, vol. 85, p: 3110, 1988).

The metal guide obtained is then introduced at the level of a skin tumour in an animal or in a human being when medical ethic conditions are present or at the level of a skin tumour in a patient suffering from skin cancer after the ablation thereof, for a conventional or extemporaneous anatomo-pathological examination.

Micro-sampling is limited to an in vivo immuno-capture and does not require specific biopsy.

Finally, the device is removed and an ELISA dosage of the FAB marker is carried out on the end of the device with a monoclonal antibody directed against the marker FAB coupled to peroxidase.

The revelation of the peroxidase activity makes it possible to deduce the expression of the marker FAP by the tumour and to modulate the therapy to be used for treating the patient at best accordingly.

What is claimed is:

1. An analysis device comprising:
    a system for at least one of a micro-invasive and a micro-sampling investigation of a substrate, said system comprising at least one metal guide including:
        a first extremity having a surface structured to define at least a series of wells to which are directly coupled at least one reactive group specific to said substrate, said first extremity being perforating, and
        a second extremity intended for handling said metal guide.

2. A device according to claim 1, further comprising a removable protection system at the level of the first extremity.

3. A device according to claim 2, wherein said removable protection system is a flexible catheter.

4. A device according to claim 1, further comprising a medical instrument having an internal opening wherein said at least one metal guide can slide.

5. A device according to claim 4, wherein said medical instrument is selected from the group comprising a transparietal aspiration needle and/or an endoscope, inclusive of an endovascular navigation system.

6. A device according to claim 5, wherein said transparietal aspiration needle is a transcutaneous or transmucosal aspiration needle.

7. A device according to claim 1, wherein said at least one metal guide is selected from the group comprising one or several flexible solid metal butts and/or one or several hollow rigid metal butts having a diameter from 0.3 to 3.5 mm and a length from $5 \times 10^{-2}$ to 2 m.

8. A device according to claim 1, wherein said at least one metal guide is associated with a visual display system on at least one part of the length thereof.

9. A device according to claim 8, wherein said visual display system is an optical fibre.

10. A device according to claim 7, wherein said at least one flexible solid metal butt is an optical fibre at a first extremity of which a metal ring provided with at least a series of wells is associated, to which at least one reactive group specific to said substrate is directly coupled, with said first extremity of said optical fibre being perforating.

11. A device according to claim 1, wherein said at least one metal guide is constituted, as a whole or in part, of a metal alloy selected from the group comprising stainless steel, titanium-, nickel-, cobalt-based alloys or a mixture thereof.

12. A device according to claim 11, wherein said metal guide is constituted, as a whole or in part, of a titanium and nickel alloy.

13. A device according to claim 1, wherein said at least one metal guide is coated, except for the first extremity, with a protective polymer layer having a thickness of $2 \times 10^{-3}$ to 1 μm.

14. A device according to claim 1, wherein said at least one reactive group is specific to a substrate or an antigen specific of cancer, an inflammation, an infection, a graft rejection or a neurodegenerative pathology.

15. A device according to claim 1, wherein said at least one reactive group specific to a substrate is an antibody or a fragment of antibody selected from the group constituted of fragments Fab, Fab', $F(ab')_2$ and Fv.

16. A tool intended for diagnosing a cancer, an inflammation, an infection, a graft rejection or a neurodegenerative pathology such as Alzheimer's disease, Parkinson's disease or an amyotrophic lateral sclerosis, the tool comprising:
    an endoscope,
    a flexible catheter configured for insertion into the endoscope, and
    at least one metal guide configured for insertion into the flexible catheter, each metal slide comprising:
        a first extremity having a surface structured to define at least a series of wells to which are directly coupled at least one reactive group specific to said substrate, said first extremity being perforating, and
        a second extremity intended for handling said metal guide.

17. The tool according to claim 16, wherein said at least one metal guide comprises a transparietal aspiration needle configured for diagnosing cancer, an inflammation, an infection, a graft rejection or a neurodegenerative pathology.

18. The tool according to claim 16, wherein said at least one metal guide and the flexible catheter cooperate so as to place the functionalized first extremity in contact with a micro-analysis and/or micro-sampling site.

19. The tool according to claim 17, wherein the transparietal aspiration needle is selected from the group consisting of a transmucosal aspiration needle and a transcutaneous aspiration needle.

20. The tool according to claim 16, wherein said at least one metal guide is associated with an optical fibre on at least a part of the length thereof.

21. A method for detecting ex-vivo a substrate existing in a tissue or an organ, comprising:
    a) providing a device comprising a system for a micro-invasive and/or micro-sampling investigation of a substrate, said system comprising at least one metal guide including:
        a first extremity having a surface defining at least a series of wells to which are directly coupled at least one reactive group specific to said substrate, said extremity being perforating, and
        a second extremity intended for handling said metal guide;
    b) incubating the functionalised first extremity of the device with a solution comprising at least one detection agent specific to said substrate when said first extremity is in contact with said tissue or organ to be examined; and
    c) detecting said substrate.

22. A method according to claim 21, wherein said at least one detection agent of step b) is a possibly marked antibody specific to said substrate.

23. A method according to claim 21, wherein a step b') of incubation of said first extremity in a solution including at least one detection agent specific of the detection agent of step b) is interposed between steps b) and c).

24. A method according to claim 23, wherein said at least one detection agent of step b') is a marked antibody specific to the detection agent of step b).

25. A method according to claim 21, wherein a step of washing follows step b).

26. A method according to claim 23 wherein a step of washing follows at least one of step b) and step b').

* * * * *